(12) United States Patent
Buehler et al.

(10) Patent No.: US 10,308,935 B2
(45) Date of Patent: Jun. 4, 2019

(54) METHODS FOR TRIGGERING DE NOVO FORMATION OF HETEROCHROMATIN AND OR EPIGENETIC SILENCING WITH SMALL RNAS

(71) Applicants: Marc Buehler, Riehen (CH); Katarzyna Kowalik, Opole (PL); Yukiko Shimada, Riehen (CH)

(72) Inventors: Marc Buehler, Riehen (CH); Katarzyna Kowalik, Opole (PL); Yukiko Shimada, Riehen (CH)

(73) Assignee: FRIEDRICH MIESCHER INSTITUTE FOR BIOMEDICAL RESEARCH, Basel (CH)

( * ) Notice: Subject to any disclaimer, the term of this patent is extended or adjusted under 35 U.S.C. 154(b) by 0 days.

(21) Appl. No.: 15/321,159

(22) PCT Filed: Jun. 22, 2015

(86) PCT No.: PCT/IB2015/054665
§ 371 (c)(1),
(2) Date: Dec. 21, 2016

(87) PCT Pub. No.: WO2015/198202
PCT Pub. Date: Dec. 30, 2015

(65) Prior Publication Data
US 2017/0152514 A1    Jun. 1, 2017

(30) Foreign Application Priority Data
Jun. 23, 2014 (EP) .................................. 14173523

(51) Int. Cl.
*C12N 15/85* (2006.01)
*C12N 15/113* (2010.01)
*A61K 31/7105* (2006.01)
*C12N 15/82* (2006.01)

(52) U.S. Cl.
CPC ........ *C12N 15/113* (2013.01); *A61K 31/7105* (2013.01); *C12N 15/8218* (2013.01); *C12N 2310/14* (2013.01)

(58) Field of Classification Search
None
See application file for complete search history.

(56) References Cited

PUBLICATIONS

Muntean et al (Cancer Cell 17, 609-621, Jun. 15, 2010) (Year: 2010).*
Van Oss et al ( Trends in Biochemical Sciences 42(10): 788-798, 2017) (Year: 2017).*
Morris (Oligonucleotides 19(4): 299-305, 2009) (Year: 2009).*
Napoli et al (EMBO J. 28, 1708-1719 (2009)) (Year: 2009).*
Clark et al (Current Biology 27, 2718-2726, 2017) (Year: 2017).*
Lin et al (Proc. Nat. Acad. Sci. USA 105(45):17420-17425, 2008) (Year: 2008).*
Tenney et al (Proc. Nat. Acad. Sci. USA 103(32):11970-11974, 2006) (Year: 2006).*
Kubota et al (Developmental Biology 391: 43-53, (Apr. 8, 2014)) (Year: 2014).*
Zhuang et al (Parasitology 139: 560-573, 2012) (Year: 2012).*
Bayne et al., "Stc1: A Critical Link between RNAi and Chromatin Modification Required for Heterochromatin Integrity", Cell, vol. 140(5), p. 666-677, (2010).
Bernstein et al., "Role for a bidentate ribonuclease in the initiation step of RNA interference", Nature, vol. 409, p. 363-366, (2001).
Buehler et al., "Tethering RITS to a Nascent Transcript Initiates RNAi- and Heterochromatin-Dependent Gene Silencing", Cell, vol. 125, p. 873-886, (2006).
Buehler et al., "Transcription and RNAi in heterochromatic gene silencing", Nature Structural & Molecular Biology, vol. 14, p. 1041-1048, (2007).
Buehler et al., "TRAMP-mediated RNA surveillance prevents spurious entry of RNAs into the Schizosaccharomyces pombe siRNA pathway", Nature Structural & Molecular Biology, vol. 15(10), p. 1015-1023, (2008).
Cam et al., "Comprehensive analysis of heterochromatin- and RNAi-mediated epigenetic control of the fission yeast genome", Nat. Genet., vol. 37(8), p. 809-819, (2005).
Castel et al., "Rna interference in the nucleus: roles for small RNAs in transcription, epigenetics and beyond", Nature reviews Genetics, vol. 14, p. 100-112, (2013).
Chan et al., "Two-Step Recruitment of RNA-Directed DNA Methylation to Tandem Repeats", PLoS Biology, vol. 4(11), p. e363, (2006).
Djupedal et al., "Epigenetics: heterochromatin meets RNAi", Cell Research, vol. 19, p. 282-295, (2009).
Fire et al., "Potent and specific genetic interference by double-stranded RNA in Caenorhabditis elegans", Nature, vol. 391, p. 806-811, (1998).
Grewel et al., "RNAi-dependent formation of heterochromatin and its diverse functions", Curr Opin Genet Dev., vol. 20(2), p. 134-141, (2010).
Gullerova et al., "Silencing in trans: position matters in fission yeast", EMBO Reports, vol. 11(3), p. 145-146, (2010).
Gullerova et al., "Convergent transcription induces transcriptional gene silencing in fission yeast and mammalian cells", Nature Structural & Molecular Biology, vol. 19(11), p. 1193-1201, (2012).
Halic et al., "Dicer-Independent Primal RNAs Trigger RNAi and Heterochromatin Formation", Cell, vol. 140(4), p. 504-516, (2010).
Hamilton et al., "A Species of Small Antisense RNA in Post-transcriptional Gene Silencing in Plants", Science, vol. 286, p. 950-952, (1999).

(Continued)

*Primary Examiner* — Richard A Schnizer
(74) *Attorney, Agent, or Firm* — Hoxie & Associates LLC

(57) ABSTRACT

The present application relates to a method for the targeted formation of heterochromatin and/or induction of epigenetic gene silencing in a cell using a small RNA, said method comprising the step of inhibiting the Paf1 complex in said cell and the step of contacting said cell with a small RNA targeted to a region of the genome of the cell, said region being the region where heterochromatin formation and/or induction of epigenetic gene silencing should be induced.

8 Claims, No Drawings

(56) References Cited

PUBLICATIONS

International Search Report of International Application No. PCT/IB2015/054665, dated Sep. 21, 2015, 2 pages.

Janowski et al., "Involvement of AGO1 and AGO2 in mammalian transcriptional silencing", Nature Structural & Molecular Biology, vol. 13(9), p. 787-792, (2006).

Jones et al., "RNA-directed transcriptional gene silencing in plants can be inherited independently of the RNA trigger and requires Met1 for maintenance", Current Biology, vol. 11(10), p. 747-757, (2001).

Joshua-Tor et al., "Ancestral Roles of Small RNAs: An Ago-Centric Perspective", Cold Spring Harb. Perspect. Biol., p. 1-11, (2011).

Kim et al., "Argonaute-1 directs siRNA-mediated transcriptional gene silencing in human cells", Nature Structural & Molecular Biology, vol. 13(9), p. 793-797, (2006).

Kim et al., "IL-1β-specific recruitment of GCN5 histone acetyltransferase induces the release of PAF1 from chromatin for the de-repression of inflammatory response genes", Nucleic Acids Research, vol. 41(8), p. 4495-4506, (2013).

Lida et al., "siRNA-meditated heterochromatin establishment requires HP1 and is associated with antisense transcription", Mol. Cell, vol. 31(2), p. 178-189, (2008).

Mette et al., "Transcriptional silencing and promoter methylation triggered by double-stranded RNA", The EMBO Journal, vol. 19(19), p. 5194-5201, (2000).

Moazed et al., "Small RNAs in transcriptional gene silencing and genome Defence", Nature, vol. 457(7228), p. 413-420, (2009).

Mochizuki et al., "Analysis of a piwi-Related Gene Implicates Small RNAs in Genome Rearrangement in Tetrahymena", Cell, vol. 110, p. 689-699, (2002).

Motamedi et al., "Two RNAi Complexes, RITS and RDRC, Physically Interact and Localize to Noncoding Centromeric RNAs", Cell, vol. 119, p. 789-802, (2004).

Muntean et al., "MLL fusion protein-driven AML is selectively inhibited by targeted disruption of the MLL-PAFc interaction", Blood, vol. 122(11), p. 1914-1922, (2013).

Peters et al., "Argonaute Proteins: Mediators of RNA Silencing", Molecular Cell, vol. 26, p. 611-623, (2007).

Reinhart et al., "Small RNAs Correspond to Centromere Heterochromatic Repeats", Science, vol. 298, p. 1831, (2002).

Schaich, T. et al., "High-Affinity Binding of Chp1 Chromodomain to K9 Methylated Histone H3 Is Required to Establish Centromeric Heterochromatin", Mol. Cell, vol. 34, p. 36-46, (2009).

Sigova et al., "A single Argonaute protein mediates both transcriptional and posttranscriptional silencing in Schizosaccharomyces pombe", Genes & Development, vol. 18, p. 2359-2367, (2004).

Simmer et al., "Hairpin RNA induces secondary small interfering RNA synthesis and silencing in trans in fission yeast", EMBO Reports, vol. 11(2), p. 112-118, (2010).

Ting et al., "Short dsRNA Induces Transcriptional Gene Silencing in Human Cancer Cells in the Absence of DNA Methylation", Nat. Gene., vol. 37(8), p. 906-910, (2005).

Verdel et al., "RNAi-Mediated Targeting of Heterochromatin by the RITS Complex", Science, vol. 303, p. 672-675, (2004).

Volpe et al., "Regulation of heterochromatic silencing and histone H3 lysine-9 methylation by RNAi", Science, vol. 297(5588), p. 1833-1837, (2002).

Volpe et al., "RNA interference is required for normal centromere function in fission yeast", Chromosome Research, vol. 11(2), p. 137-146, (2003).

Yu et al., "Determinants of Heterochromatic siRNA Biogenesis and Function", Molecular Cell, vol. 53, p. 262-276, (2014).

Zamore et al., "RNAi: Double-Stranded RNA Directs the ATP-Dependent Cleavage of mRNA at 21 to 23 Nucleotide Intervals", Cell, vol. 101, p. 25-33, (2000).

\* cited by examiner

METHODS FOR TRIGGERING DE NOVO FORMATION OF HETEROCHROMATIN AND OR EPIGENETIC SILENCING WITH SMALL RNAS

CROSS REFERENCE TO RELATED APPLICATIONS

This application is a United States Application under 35 U.S.C. 371 claiming benefit of PCT Application No. PCT/IB2015/054665, filed on Jun. 22, 2015, which claims the benefit of European Application No. 14173523.3, filed on Jun. 23, 2014, the contents of each of which are incorporated herein by reference.

The present invention relates to methods for targeted de novo formation of heterochromatin and/or induction of epigenetic gene silencing.

RNA interference (RNAi) refers to the ability of exogenously introduced double-stranded RNA (dsRNA) to silence expression of homologous sequences (Fire, A. et al, Nature 391, 806-811 (1998)). Silencing is initiated when Dicer processes the dsRNA into small interfering RNAs (siRNAs) (Zamore, P. D., Tuschl, T., Sharp, P. A. & Bartel, D. P. Cell 101, 25-33 (2000); Hamilton, A. J. & Baulcombe, D. C. Science 286, 950-952 (1999); Bernstein, E., Caudy, A. A., Hammond, S. M. & Hannon, G. J. Nature 409, 363-366 (2001)). siRNAs are incorporated into Argonaute protein-containing effector complexes, which they guide to complementary targets. Depending on the protein composition of the effector complex, different types of silencing can occur (Joshua-Tor, L. & Hannon, G. J. Cold Spring Harb Perspect Biol 3, a003772, doi:10.1101/cshperspect.a003772 (2011); Peters, L. & Meister, G. Mol Cell 26, 611-623, doi:S1097-2765(07)00257-2 [pii] 10.1016/j.molcel.2007.05.001 (2007)). siRNAs are potent inducers of mRNA degradation in the cytoplasm of plant and animal cells and are widely used to reduce expression of specific genes of interest in experimental biology and biotechnology. In addition to functioning in post-transcriptional gene silencing (PTGS), siRNAs have also been implicated in DNA methylation and chromatin modification in organisms of all eukaryotic kingdoms (Volpe, T. A. et al. Science 297, 1833-1837 (2002); Mochizuki, K., Fine, N. A., Fujisawa, T. & Gorovsky, M. A. Cell 110, 689-699 (2002); Mette, M. F., Aufsatz, W., van der Winden, J., Matzke, M. A. & Matzke, A. J. EMBO J 19, 5194-5201, doi:10.1093/emboj/19.19.5194 (2000); Kim, D. H., Villeneuve, L. M., Morris, K. V. & Rossi, J. J. Argonaute-1 directs siRNA-mediated transcriptional gene silencing in human cells. Nat Struct Mol Biol 13, 793-797, doi:nsmb1142 [pii] 10.1038/nsmb1142 (2006)). Such chromatin-dependent gene silencing (CDGS) is potentially a more stable means to silence genes than PTGS because repression may be maintained even if the primary siRNA signal is temporarily removed (Mette, M. F., Aufsatz, W., van der Winden, J., Matzke, M. A. & Matzke, A. J. EMBO J 19, 5194-5201, doi:10.1093/emboj/19.19.5194 (2000); Kim, D. H., Villeneuve, L. M., Morris, K. V. & Rossi, J. J. Nat Struct Mol Biol 13, 793-797, doi:nsmb1142 [pii] 10.1038/nsmb1142 (2006); Jones, L., Ratcliff, F. & Baulcombe, D. C. Curr. Biol. 11, 747-757 (2001)). However, our understanding of the mechanisms that allow some siRNAs to act on chromatin, and restrict other siRNAs to PTGS, is limited (Moazed, D. Nature 457, 413-420, doi:10.1038/nature07756 (2009)).

In the fission yeast Schizosacharomyces pombe, a functional RNAi pathway is required for the formation and stable propagation of constitutive heterochromatin that is found at pericentromeric repeat sequences. S. pombe contains single genes encoding for an Argonaute and a Dicer protein, called ago1+ and dcr1+, respectively. Centromeres of ago/delta or dcrldelta cells have markedly reduced H3K9 methylation, causing chromosome segregation problems and loss of heterochromatic gene silencing (Volpe, T. A. et al. Science 297, 1833-1837 (2002); Volpe, T. et al. Chromosome Res 11, 137-146 (2003)). Ago1 is loaded with endogenous small RNAs that correspond to heterochromatic repeats and interacts with Chp1 and Tas3 to form the RNA-induced transcriptional silencing (RITS) complex (Halic, M. & Moazed, D. Cell 140, 504-516, doi:S0092-8674(10)00020-6 [pii] 10.1016/j.cell.2010.01.019 (2010); Cam, H. P. et al. Nat. Genet 37, 809-819 (2005); Reinhart, B. J. & Bartel, D. P. Science 297, 1831 (2002); Verdel, A. et al. R. Science 303, 672-676 (2004); Buhler, M., Spies, N., Bartel, D. P. & Moazed, D. Nat Struct Mol Biol 15, 1015-1023, doi:nsmb.1481 [pii]10.1038/nsmb.1481 (2008)). Chp1 contains a chromodomain that binds methylated H3K9, a hallmark of heterochromatin, with high affinity (Schalch, T. et al. Mol Cell 34, 36-46, doi:S1097-2765(09)00140-3 [pii]10.1016/j.molce1.2009.02.024 (2009)). Thus, RITS constitutes a programmable bivalent complex with affinities for both heterochromatin and nucleic acids.

Current models propose that Ago1-bound small RNAs function as specificity factors to target RITS to centromeres via base-paring interactions with nascent, chromatin-associated non-coding transcripts. Consequently, RITS recruits the RNA-dependent RNA polymerase complex (RDRC) to initiate dsRNA synthesis and siRNA amplification, as well as the cryptic loci regulator complex (CLRC) to facilitate methylation of histone H3K9 (Motamedi, M. R. et al. Cell 119, 789-802 (2004); Bayne, E. H. et al. Cell 140, 666-677, doi:10.1016/j.cell.2010.01.038 (2010)). Chp1 reinforces heterochromatin association of RITS, thereby creating a positive-feedback loop between siRNA biogenesis, RITS localization, and H3K9 methylation (Buhler, M. & Moazed, D. Nat. Struct. Mol Biol. 14, 1041-1048 (2007); Castel, S. E. & Martienssen, R. A. Nature reviews. Genetics 14, 100-112, doi:10.1038/nrg3355 (2013); Grewal, S. I. Current opinion in genetics & development 20, 134-141, doi:10.1016/j.gde.2010.02.003 (2010); Djupedal, I. & Ekwall, K. Cell Res 19, 282-295, doi:cr200913 [pii]10.1038/cr.2009.13 (2009)). Hence, siRNA-programmed RITS acts as a specificity determinant for the recruitment of other RNAi complexes and chromatin-modifying enzymes to centromeres. However, an outstanding question is whether synthetic siRNAs can be used to trigger de novo formation of heterochromatin outside centromeric repeats at will (Moazed, D. Nature 457, 413-420, doi:10.1038/nature07756 (2009); Gullerova, M. & Proudfoot, N. J. EMBO reports 11, 145-146, doi:10.1038/embor.2010.24 (2010)). Although endogenous siRNAs are important components of some CDGS mechanisms, efforts to initiate chromatin modifications in trans by using siRNAs have been inherently difficult to achieve in eukaryotic cells. The ability of siRNAs to promote DNA methylation in plants is context-dependent and sensitive to pre-existing chromatin modifications (Chan, S. W., Zhang, X., Bernatavichute, Y. V. & Jacobsen, S. E. PLoS. Biol. 4, e363 (2006)). It is also unclear how commonly synthetic siRNAs would trigger the methylation of endogenous promoters, although siRNAs have been shown to promote DNA methylation in trans on homologous reporter transgenes in Tobacco and Arabidopsis (Mette, M. F., Aufsatz, W., van der Winden, J., Matzke, M. A. & Matzke, A. J. EMBO J 19, 5194-5201, doi:10.1093/emboj/19.19.5194 (2000)). In animal cells, most siRNAs do not appear to act on chromatin and siRNA-mediated chromatin modifications reported in mammalian cells are variable (Ting, A. H., Schuebel, K. E., Herman, J. G. & Baylin, S. B. *Nat Genet* 37, 906-910, doi:ng1611 [pii]10.1038/ng1611 (2005); Janowski, B. A. et al. *Nat Struct Mol Biol* 13, 787-792, doi:nsmb1140 [pii]10.1038/nsmb1140 (2006)). Similarly, although studies in *S. pombe* have shown that ectopically produced siRNAs have the potential to promote H3K9 methylation in trans at some loci (Gullerova, M. & Proudfoot, N. J. *Nature structural & molecular biology* 19, 1193-1201, doi:10.1038/nsmb.2392 (2012); Simmer, F. et al. *EMBO reports* 11, 112-118, doi:10.1038/embor.2009.273 (2010); Iida, T., Nakayama, J. & Moazed, D. *Mol Cell* 31, 178-189, doi:S1097-2765(08)00464-4 [pii]10.1016/j.molcel.2008.07.003 (2008); Buhler, M., Verdel, A. & Moazed, D. *Cell* 125, 873-886 (2006)), it is very inefficient and the silent state observed is weak and highly unstable (Simmer, F. et al. *EMBO reports* 11, 112-118, doi:10.1038/embor.2009.273 (2010); Sigova, A., Rhind, N. & Zamore, P. D. *Genes Dev.* 18, 2359-2367 (2004)). Rather, endogenous protein-coding genes such as ura4+ appear to be refractory to siRNA-directed repression in wild type cells (Simmer, F. et al. *EMBO reports* 11, 112-118, doi:10.1038/embor.2009.273 (2010); Iida, T., Nakayama, J. & Moazed, D. *Mol Cell* 31, 178-189, doi:S1097-2765(08)00464-4 [pii] 10.1016/j.molcel.2008.07.003 (2008); Yu, R., Jih, G., Iglesias, N. & Moazed, D. *Molecular cell* 53, 262-276, doi: 10.1016/j.molcel.2013.11.014 (2014)). Therefore, there is a need in the art for a method that would allow for siRNAs to direct de novo formation of heterochromatin (in trans).

The present inventors discovered that small RNAs are highly effective in directing the assembly of heterochromatin that can be stably maintained through mitosis and meiosis if Paf1C activity is impaired. A remarkable observation is that the newly established heterochromatin was inherited for hundreds of generations in Paf1C mutant cells, even in the absence of the primary small RNAs that triggered the assembly of heterochromatin. This phenomenon complies with the classical definition of epigenetics and highlights fundamental roles of Paf1C and the RNAi machinery in building up epigenetic memory.

The present invention hence provides a method for the targeted formation of heterochromatin and/or induction of epigenetic gene silencing in a cell using a small RNA, said method comprising the step of inhibiting the Paf1 complex, for instance by inhibiting one of its sub-units Paf1, Cdc73, Ctr9, Rtf1, or Leo1, in said cell and the step of contacting said cell with a small RNA targeted to a region of the genome of the cell, said region being the region where heterochromatin formation and/or induction of epigenetic gene silencing should be induced. The method of the invention can be carried out in vivo, in vitro or ex vivo. In some embodiments, the step of inhibiting the Paf1 complex comprises the step of modifying at least one gene of a component of the Paf1 complex in such a way that the activity of said complex is reduced. In some embodiments, the component of the Paf1 complex Leo1 is inhibited. In some embodiments, the step of inhibiting the Paf1 complex comprises the step of selecting a mutant cell in which at least one gene of a component of the Paf1 complex is mutated in such a way that the activity of said complex is reduced. In some embodiments, said mutant is a naturally-occurring mutant. The present invention also provides a modulator of the Paf1 complex for use in the targeted formation of heterochromatin in a cell using a small RNA. In some embodiments, the modulator is an isolated nucleic acid molecule comprising a nucleotide sequence coding for miRNA against a component of the Paf1 complex, for instance Leo1.

The present invention also provides the use of a modulator of the Paf1 complex for the targeted formation of heterochromatin in a cell using a small RNA. In some embodiments, the modulator is an isolated nucleic acid molecule comprising a nucleotide sequence coding for miRNA against a component of the Paf1 complex, for instance Leo1. The modulator can be a specific binding molecule, such as an oligonucleotide probe, antibody, or aptamer.

In some embodiments, the cell is a plant cell, for example a cell from a plant tissue or from a seed. In some embodiments, the plant is selected from the group of species of woody, ornamental or decorative, crop or cereal, fruit or vegetable plant, and algae (e.g., *Chlamydomonas reinhardtii*). Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia*. Still other examples of plants include, but are not limited to, wheat, cauliflower, tomato, tobacco, corn, petunia, trees, etc.

In some embodiments, the cell is from an animal, including but not limited to animals such as mammals, e.g. cows, pigs, horses, chickens, cats, dogs, primates, camels etc., and is in some embodiments, a mammal, for example human. In some embodiments, the cell is from an animal but not from a human. In some embodiment, the cell is selected from bacteria, yeast or funghi cells. In some embodiments, the cell is an insect cell.

The methods of the invention can, for instance, be used to switch off mutated genes. In some cases, said genes have a dominant negative mutation, Dominant negative mutations (also called antimorphic mutations) have an altered gene product that acts antagonistically to the wild-type allele. These mutations usually result in an altered molecular function (often inactive) and are characterized by a dominant or semi-dominant phenotype. In humans, dominant negative mutations have been implicated in cancer (e.g., mutations in genes p53, ATM, CEBPA and PPARgamma). In one embodiment, the invention provides hence a method to treat a disease such as cancer in a cell, said method using a small RNA, and comprising the step of inhibiting the Paf1 complex in said cell and the step of contacting said cell with a small RNA targeted to a region of the genome of the cell harbouring a mutated gene, for instance a dominant negative mutation. In some embodiments, said disease is a cancer.

"Small RNAs" (sRNA) are small (18-30 nucleotide) non-coding RNA molecules. Their precursors are generally are highly structured and often contain several stem-loops. For the purpose of the present invention, sRNA includes highly abundant and functionally important RNAs such as snoRNAs, microRNAs, siRNAs, snRNAs, exRNAs, and piRNAs.

By "altered expression" we include where the gene expression is either elevated or reduced in the sample when compared to a control. Conversely by "unaltered expression" we include where the gene expression is not elevated or reduced in the sample when compared to the control, as discussed above.

An assessment of the levels of a miRNA and of whether a gene expression is altered or unaltered can be made using routine methods of statistical analysis.

It will be understood that "nucleic acids" or "nucleic acid molecules" for the purposes of the present invention refer to deoxyribonucleotide or ribonucleotide polymers in either single—or double—stranded form. Furthermore, unless the context requires otherwise, these terms should be taken to encompass known analogues of natural nucleotides that can function in a similar manner to naturally occurring nucleotides.

Furthermore it will be understood that target nucleic acids suitable for use in accordance with the invention need not comprise "full length" nucleic acids (e.g. full length gene transcripts), but need merely comprise a sufficient length to allow specific binding of molecules.

In the case of assessing the expression of chosen gene, it may be preferred that RNA derived from a subject or control sample may be used as substrate for cDNA synthesis, for example using the Superscript System (Invitrogen Corp.). The resulting cDNA may then be converted to biotinylated cRNA using the BioArray RNA Transcript labelling Kit (Enzo Life Sciences Inc.) and this cRNA purified from the reaction mixture using an RNeasy mini kit (Qiagen Ltd). mRNA, representative of gene expression, may be measured directly in a tissue derived from a subject or control sample, without the need for mRNA extraction or purification. For example, mRNA present in, and representative of gene expression in, a subject or control sample of interest may be investigated using appropriately fixed sections or biopsies of such a tissue. The use of samples of this kind may provide benefits in terms of the rapidity with which comparisons of expression can be made, as well as the relatively cheap and simple tissue processing that may be used to produce the sample. In situ hybridisation techniques represent preferred methods by which gene expression may be investigated and compared in tissue samples of this kind. Techniques for the processing of tissues of interest that maintain the availability of RNA representative of gene expression in the subject or control sample are well known to those of skill in the art. However, techniques by which mRNAs representative of gene expression in a subject or control sample may be extracted and collected are also well known to those skilled in the art, and the inventors have found that such techniques may be advantageously employed in accordance with the present invention. Samples comprising extracted mRNA from a subject or control sample may be preferred for use in the method of the third aspect of the invention, since such extracts tend to be more readily investigated than is the case for samples comprising the original tissues. For example, suitable target molecules allowing for comparison of gene expression may comprise the total RNA isolated from a sample of tissue from the subject, or a sample of control tissue. Furthermore, extracted RNA may be readily amplified to produce an enlarged mRNA sample capable of yielding increased information on gene expression in the subject or control sample. Suitable examples of techniques for the extraction and amplification of mRNA populations are well known, and are considered in more detail below.

By way of example, methods of isolation and purification of nucleic acids to produce nucleic acid targets suitable for use in accordance with the invention are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993).

In the event that it is desired to amplify the nucleic acid targets prior to investigation and comparison of gene expression it may be preferred to use a method that maintains or controls for the relative frequencies of the amplified nucleic acids in the subject or control tissue from which the sample is derived.

Suitable methods of "quantitative" amplification are well known to those of skill in the art. One well known example, quantitative PCR, involves simultaneously co-amplifying a control sequence whose quantities are known to be unchanged between control and subject samples. This provides an internal standard that may be used to calibrate the PCR reaction.

In addition to the methods outlined above, the skilled person will appreciate that any technology coupling the amplification of gene-transcript specific product to the generation of a signal may also be suitable for quantitation. A preferred example employs convenient improvements to the polymerase chain reaction (U.S. Pat. Nos. 4,683,195 and 4,683,202) that have rendered it suitable for the exact quantitation of specific mRNA transcripts by incorporating an initial reverse transcription of mRNA to cDNA. Further key improvements enable the measurement of accumulating PCR products in real-time as the reaction progresses.

In many cases it may be preferred to assess the degree of gene expression in subject or control samples using probe molecules capable of indicating the presence of target molecules in the relevant sample.

Probes may be selected with reference to the product (direct or indirect) of gene expression to be investigated. Examples of suitable probes include oligonucleotide probes, antibodies, aptamers, and binding proteins or small molecules having suitable specificity.

Oligonucleotide probes can be used as probes. The generation of suitable oligonucleotide probes is well known to those skilled in the art (Oligonucleotide synthesis: Methods and Applications, Piet Herdewijn (ed) Humana Press (2004)). Oligonucleotide and modified oligonucleotides are commercially available from numerous companies.

For the purposes of the present description, an oligonucleotide probe may be taken to comprise an oligonucleotide capable of hybridising specifically to a nucleic acid target molecule of complementary sequence through one or more types of chemical bond. Such binding may usually occur through complementary base pairing, and usually through hydrogen bond formation. Suitable oligonucleotide probes may include natural (i.e., A, G, C, or T) or modified bases (7-deazaguanosine, inosine, etc.). In addition, a linkage other than a phosphodiester bond may be used to join the bases in the oligonucleotide probe(s), so long as this variation does not interfere with hybridisation of the oligonucleotide probe to its target. Thus, suitable oligonucleotide probes may be peptide nucleic acids in which the constituent bases are joined by peptide bonds rather than phosphodiester linkages.

As explained herein, microRNA molecules ("miRNAs") are generally 21 to 22 nucleotides in length, though lengths of 17 and up to 25 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals. Dicer is ribonuclease III-like nuclease. The processed miRNA is typically a portion of the stem.

The processed miRNA (also referred to as "mature miRNA") become part of a large complex to down-regulate a particular target gene. Examples of animal miRNAs include those that imperfectly basepair with the target, which halts translation (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

Synthetic miRNAs of the invention comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, called the synthetic miRNA, that is similar to the naturally occurring miRNA precursor that is bound by the protein complex immediately prior to miRNA activation in the cell. Maximizing activity of the synthetic miRNA requires maximizing uptake of the active strand and minimizing uptake of the complementary strand by the miRNA protein complex that regulates gene expression at the level of translation. The molecular designs that provide optimal miRNA activity involve modifications to the complementary strand. Two designs incorporate chemical modifications in the complementary strand. The first modification involves creating a complementary RNA with a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others. The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance synthetic miRNA activities.

A third synthetic miRNA design involves incorporating nucleotides in the 3' end of the complementary strand that are not complementary to the active strand.

Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The judicious use of mismatches in the complementary RNA strand significantly enhances the activity of the synthetic miRNA.

As explained herein, the term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

Synthetic miRNAs typically comprise two strands, an active strand that is identical in sequence to the mature miRNA that is being studied and a complemenrtary strand that is at least partially complementary to the active strand. The active strand is the biologically relevant molecule and should be preferentially taken up by the complex in cells that modulates translation either through mRNA degradation or translational control. Preferential uptake of the active strand has two profound results:

(1) the observed activity of the synthetic miRNA increases dramatically and (2) non-intended effects induced by uptake and activation of the complementary strand are essentially eliminated. According to the invention, several synthetic miRNA designs can be used to ensure the preferential uptake of the active strand.

The introduction of a stable moiety other than phosphate or hydroxyl at the 5' end of the complementary strand impairs its activity in the miRNA pathway. This ensures that only the active strand of the synthetic miRNA will be used to regulate translation in the cell. 5' modifications include, but are not limited to, NH2, biotin, an amine group, a lower alkylamine group, an acetyl group, 2 O-Me, DMTO, fluoroscein, a thiol, or acridine or any other group with this type of functionality.

Other sense strand modifications. The introduction of nucleotide modifications like 2'-0Me, NH2, biotin, an amine group, a lower alkylamine group, an acetyl group, DMTO, fluoroscein, a thiol, or acridine or any other group with this type of functionality in the complementary strand of the synthetic miRNA can eliminate the activity of the complementary strand and enhance uptake of the active strand of the miRNA.

As with siRNAs (Schwarz 2003), the relative stability of the 5' and 3' ends of the active strand of the synthetic miRNA apparently determines the uptake and activation of the active by the miRNA pathway. Destabilizing the 5' end of the active strand of the synthetic miRNA by the strategic placement of base mismatches in the 3' end of the complementary strand of the synthetic miRNA enhances the activity of the active strand and essentially eliminates the activity of the complementary strand.

The phrase "hybridising specifically to" as used herein refers to the binding, duplexing, or hybridising of an oligonucleotide probe preferentially to a particular target nucleotide sequence under stringent conditions when that sequence is present in a complex mixture (such as total cellular DNA or RNA). In one embodiment, a probe may bind, duplex or hybridise only to the particular target molecule.

The term "stringent conditions" refers to conditions under which a probe will hybridise to its target subsequence, but minimally to other sequences. In some embodiments, a probe may hybridise to no sequences other than its target under stringent conditions. Stringent conditions are sequence-dependent and will be different in different circumstances. Longer sequences hybridise specifically at higher temperatures.

In general, stringent conditions may be selected to be about 5° C. lower than the thermal melting point (Tm) for the specific sequence at a defined ionic strength and pH. The Tm is the temperature (under defined ionic strength, pH, and nucleic acid concentration) at which 50% of the oligonucleotide probes complementary to a target nucleic acid hybridise to the target nucleic acid at equilibrium. As the target nucleic acids will generally be present in excess, at Tm, 50% of the probes are occupied at equilibrium. By way of example, stringent conditions will be those in which the salt concentration is at least about 0.01 to 1.0 M $Na^+$ ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

Gene expression in a sample representing gene expression and/or levels of miRNAs in a subject may be assessed with reference to global transcript levels within suitable nucleic acid samples by means of high-density oligonucleotide array technology. Such technologies make use of arrays in which oligonucleotide probes are tethered, for example by covalent attachment, to a solid support. These arrays of oligonucleotide probes immobilized on solid supports represent preferred components to be used in the methods and kits of the invention for the comparison of gene expression. Large numbers of such probes may be attached in this manner to provide arrays suitable for the comparison of expression of large numbers of genes or miRNAs. Accordingly it will be recognised that such oligonucleotide arrays may be particularly preferred in embodiments where it is desired to compare expression of more than one miRNA and/or gene.

Other suitable methodologies that may be used in the comparison of nucleic acid targets representative of gene expression include, but are not limited to, nucleic acid sequence based amplification (NASBA); or rolling circle DNA amplification (RCA).

It is usually desirable to label probes in order that they may be easily detected. Examples of detectable moieties that may be used in the labelling of probes or targets suitable for use in accordance with the invention include any composition detectable by spectroscopic, photochemical, biochemical, immunochemical, electrical, optical or chemical means. Suitable detectable moieties include various enzymes, prosthetic groups, fluorescent materials, luminescent materials, bioluminescent materials, radioactive materials and colorimetric materials. These detectable moieties are suitable for incorporation in all types of probes or targets that may be used in the methods of the invention unless indicated to the contrary.

Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, phycoerythrin, texas red, rhodamine, green fluorescent protein, and the like; an example of a luminescent material includes luminol; examples of bioluminescent materials include luciferase, luciferin, and aequorin; examples of suitable radioactive material include $^{125}I$, $^{131}I$, $^{35}S$, $^{3}H$, $^{14}C$, or $^{32}P$; examples of suitable colorimetric materials include colloidal gold or coloured glass or plastic (e.g., polystyrene, polypropylene, latex, etc.) beads. Means of detecting such labels are well known to the skilled person. For example, radiolabels may be detected using photographic film or scintillation counters; fluorescent markers may be detected using a photodetector to detect emitted light.

Enzymatic labels are typically detected by providing the enzyme with a substrate and detecting the reaction product produced by the action of the enzyme on the substrate, and colorimetric labels are detected by simply visualizing the coloured label.

Antibodies according to the present description include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), single-domain antibodies (sdAb, also called nanobodies), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In addition, in the context of the present invention, the term "antibody" shall also encompass alternative molecules having the same function, e.g. ankyrin repeats, aptamers and/or CDRs grafted onto alternative peptidic or non-peptidic frames. In some embodiments the antibodies are human antigen-binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CHI, CH2, and CH3 domains. Also included in the description are antigen-binding fragments also comprising any combination of variable region(s) with a hinge region, CHI, CH2, and CH3 domains. The antibodies of the present description may be from any animal origin including birds and mammals. In some embodiments, the antibodies are human, murine (e.g., mouse and rat), donkey, ship rabbit, goat, guinea pig, camel, shark, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al. The antibodies of the present invention may be monospecific, bispecific, trispecific or of greater multi specificity.

Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992).

Antibodies of the present description may be described or specified in terms of the epitope(s) or portion(s) of a polypeptide which they recognize or specifically bind. The epitope(s) or polypeptide portion(s) may be specified as described herein, e.g., by N-terminal and C-terminal positions, by size in contiguous amino acid residues. Antibodies may also be described or specified in terms of their cross-reactivity. Antibodies that do not bind any other analog, ortholog, or homolog of a polypeptide of the present description are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide are also included in the present invention. In specific embodiments, antibodies cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide are also included in the present description).

Antibodies may also be described or specified in terms of their binding affinity to a polypeptide. Antibodies may act as agonists or antagonists of the recognized polypeptides. The present description also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The present description also features receptor-specific antibodies which both prevent ligand binding and receptor activation, for instance an antibody against Leo1, as well as antibodies that recognize the Paf1 complex. Likewise, encompassed by the invention are antibodies which bind the ligand, thereby preventing receptor activation, but do not prevent the ligand from binding the receptor. The antibodies may be specified as agonists, antagonists or inverse agonists for biological activities comprising the specific biological activities of the peptides disclosed herein. The above antibodies can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9):1153-1167 (1998); Bartunek et al., Cytokine 8(I):14-20 (1996).

As discussed in more detail below, the antibodies may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396, 387. The antibodies as defined for the present invention include derivatives that are modified, i. e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present description may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen.

Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvurn*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. As described in these references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax. et al., BioTechniques 12(6):864-869 (1992); and Sawai et al., AJRI 34:26-34 (1995); and Better et al., Science 240:1041-1043 (1988).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, and/or improve, antigen binding. These framework substitutions are identified by methods well known in the art, e.g., by modelling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988).) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592, 106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741. Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immurnol. 13:65-93 (1995). For a detailed discussion of this technology for producing human antibodies and human monoclonal antibodies and protocols for producing such antibodies, see, e. g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Freemont, Calif.) and Genpharm (San Jose, Calif.) can be engaged to provide human antibodies directed against a selected antigen using technology similar to that described above. Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)). Furthermore, antibodies can be utilized to generate anti-idiotype antibodies that "mimic" polypeptides using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization. and/or binding of a polypeptide to a ligand can be used to generate anti-idiotypes that "mimic" the polypeptide multimerization. and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide and/or to bind its ligands/receptors, and thereby block its biological activity. Polynucleotides encoding antibodies, comprising a nucleotide sequence encoding an antibody are also encompassed. These polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

The amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and in some embodiments, human framework regions (see, e.g., Chothia et al., J. Mol. Biol. 278: 457-479 (1998) for a listing of human framework regions). In some embodiments, the polynucleotide generated by the combination of the framework regions and CDRs encodes an antibody that specifically binds a polypeptide. In some embodiments, as discussed supra, one or more amino acid substitutions may be made within the framework regions, and, in some embodiments, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polymicleotide are encompassed by the present description and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)). The present invention encompasses antibodies recombinantly fused or chemically conjugated (including both covalently and non-covalently conjugations) to a polypeptide (or portion thereof, in some embodiments, at least 10, 20, 30, 40, 50, 60, 70, 80, 90 or 100 amino acids of the polypeptide) to generate fusion proteins. The fusion does not necessarily need to be direct, but may occur through linker sequences. The antibodies may be specific for antigens other than polypeptides (or portion thereof, in some embodiments, at least 10, 20, 30, 40, 50, 60, 70, 80, 90 or 100 amino acids of the polypeptide). Further, an antibody or fragment thereof may be conjugated to a therapeutic moiety, for instance to increase their therapeutical activity. The conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, B-interferon, nerve growth factor, platelet derived growth factor, tissue plasminogen activator, an apoptotic agent, e.g., TNF-alpha, TNF-beta, AIM I (See, International Publication No. WO 97/33899), AIM 11 (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 interleukin-2 ("IL-2"), interleukin-6 ("IL-6"), granulocyte macrophage colony stimulating factor ("GM-CSF"), granulocyte colony stimulating factor ("G-CSF"), or other growth factors. Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982). Alternatively, an antibody can be conjugated to a second antibody to form an antibody heteroconjugate as described by Segal in U.S. Pat. No. 4,676,980.

The present invention is also directed to antibody-based therapies which involve administering antibodies of the invention to an animal, in some embodiments, a mammal, for example a human, patient to treat diseases. Therapeutic compounds include, but are not limited to, antibodies (including fragments, analogs and derivatives thereof as described herein) and nucleic acids encoding antibodies of the invention (including fragments, analogs and derivatives thereof and anti-idiotypic antibodies as described herein).

Antibodies of the invention may be provided in pharmaceutically acceptable compositions as known in the art or as described herein.

In some embodiments, said inhibitory compound is a small molecule, an antibody or a siRNA. In an embodiment, the compound is substantially purified (e.g., substantially free from substances that limit its effect or produce undesired side-effects).

In some embodiments, the cell is from an animal, including but not limited to animals such as cows, pigs, horses, chickens, cats, dogs, etc., and is in some embodiments, a mammal, for example human.

In some embodiments, the cell is from an animal but not from a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound, e.g., encapsulation in liposomes, microparticles, microcapsules, recombinant cells capable of expressing the compound, receptor-mediated endocytosis (see, e. g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.) In yet another embodiment, the compound or composition can be delivered in a controlled release system. In one embodiment, a pump may be used (see Langer, supra; Sefton, CRC Crit. Ref, Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g. Goodson, in Medical Applications of Controlled Release, supra, vol. 2, pp. 115-13 8 (1984)). Other controlled release systems are discussed in the review by Langer (Science 249:1527-1533 (1990)).

The present invention also provides pharmaceutical compositions for use in the treatment of influenza. Such compositions comprise a therapeutically effective amount of an inhibitory compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, driied skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, in some embodiments, in purified form, together with a suitable amount of carrier so as to provide the form for proper administration to the patient. The formulation should suit the mode of administration.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lidocaine to ease pain at the site of the injection.

Generally, the ingredients are supplied either separately or mixed together in unit dosage form, for example, as a dry lyophilized powder or water free concentrate in a hermetically sealed container such as an ampoule or sachette indicating the quantity of active agent.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. The amount of the compound which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patients circumstances.

Effective doses may be extrapolated from dose-response curves derived from in vitro or animal model test systems. For antibodies, the dosage administered to a patient is typically 0.1 mg/kg to 100 mg/kg of the patients body weight. In some embodiments, the dosage administered to a patient is between 0.1 mg/kg and 20 mg/kg of the patients body weight, for example 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

Also encompassed is a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The antibodies as encompassed herein may also be chemically modified derivatives which may provide additional advantages such as increased solubility, stability and circulating time of the polypeptide, or decreased immunogenicity (see U.S. Pat. No. 4,179,337). The chemical moieties for derivatisation may be selected from water soluble polymers such as polyethylene glycol, ethylene glycol/propylene glycol copolymers, carboxymethyl cellulose, dextran, polyvinyl alcohol and the like. The antibodies may be modified at random positions within the molecule, or at predetermined positions within the molecule and may include one, two, three or more attached chemical moieties. The polymer may be of any molecular weight, and may be branched or unbranched. For polyethylene glycol, the preferred molecular weight is between about 1 kDa and about 100000 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,600, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999). The polyethylene glycol molecules (or other chemical moieties) should be attached to the protein with consideration of effects on functional or antigenic domains of the protein. There are a number of attachment methods available to those skilled in the art, e.g., EP 0 401 384 (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. As suggested above, polyethylene glycol may be attached to proteins via linkage to any of a number of amino acid residues. For example, polyethylene glycol can be linked to proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein. As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466.

In some embodiment, the cell is from, or in, a plant.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

As used herein, the term plant is also used in its broadest sense, including, but is not limited to, any species of woody, ornamental or decorative, crop or cereal, fruit or vegetable plant, and algae (e.g., *Chlamydomonas reinhardtii*). Non-limiting examples of plants include plants from the genus *Arabidopsis* or the genus *Oryza*. Other examples include plants from the genuses *Acorus, Aegilops, Allium, Ambo-rella, Antirrhinum, Apium, Arachis, Beta, Betula, Brassica, Capsicum, Ceratopteris, Citrus, Cryptomeria, Cycas, Des-curainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Per-sea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*. Still other examples of plants include, but are not limited to, wheat, cauliflower, tomato, tobacco, corn, petunia, trees, etc. As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce.

The term "plant part" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture. The aforementioned term also includes plant products, such as grain, fruits, and nuts.

The term "plant organ" refers to plant tissue or group of tissues that constitute a morphologically and functionally distinct part of a plant.

Paf1, RNA Polymerase II Associated Factor, Homolog (*S. Cerevisiae*), also known as Paf1, PD2, Pancreatic Differentiation Protein 2, F23149_1, RNA Polymerase II-Associated Factor 1 Homolog, or hPAF1, is a component of the PAF1 complex (PAF1C) which has multiple functions during transcription by RNA polymerase II and is implicated in regulation of development and maintenance of embryonic stem cell pluripotency. PAF1C associates with RNA polymerase II through interaction with POLR2A CTD non-phosphorylated and 'Ser-2'- and 'Ser-5'-phosphorylated forms and is involved in transcriptional elongation, acting both indepently and synergistically with TCEA1 and in cooperation with the DSIF complex and HTATSF1. PAF1C is required for transcription of Hox and Wnt target genes. PAF1C is involved in hematopoiesis and stimulates transcriptional activity of KMT2A/MLL1; it promotes leukemogenesis through association with KMT2A/MLL1-rearranged oncoproteins, such as KMT2A/MLL1-MLLT3/AF9 and KMT2A/MLL1-MLLT1/ENL. PAF1C is involved in histone modifications such as ubiquitination of histone H2B and methylation on histone H3 'Lys-4' (H3K4me3). PAF1C recruits the RNF20/40 E3 ubiquitin-protein ligase complex and the E2 enzyme UBE2A or UBE2B to chromatin which mediate monoubiquitination of 'Lys-120' of histone H2B (H2BK120ub1); UB2A/B-mediated H2B ubiquitination is proposed to be coupled to transcription. PAF1C is involved in mRNA 3' end formation probably through association with cleavage and poly(A) factors. In case of infection by influenza A strain H3N2, PAF1C associates with viral NS1 protein, thereby regulating gene transcription. Connects PAF1C with the RNF20/40 E3 ubiquitin-protein ligase complex. Paf1 is also involved in polyadenylation of mRNA precursors.

The Paf1 complex (Paf1C) was originally characterized as a collection of proteins associated with the unphosphorylated form of Pol II (Wade et al., 1996). Paf1 and Cdc73 were among the first factors identified in this complex, and they were shown to associate with Pol II and the GTFs TFIIB and TFIIF in a form biochemically distinct from the Srb/MedC (Shi et al. 1996 and Shi et al. 199)7. Recently, Ctr9, Rtf1, and Leo1 were identified as additional components of Paf1C (Koch et al. 1999, Krogan et al. 2002, Mueller and Jaehning 2002 and Squazzo et al. 2002). Based on the association with unphosphorylated Pol II and GTFs, the fact that Paf1C genes are nonessential (Shi et al. 1996, Shi et al. 1997 and Stolinski et al. 1997), and the observation that loss of Paf1 factors results in altered abundance of only a subset of yeast transcripts (Chang et al. 1999 and Porter et al. 2002), it was originally hypothesized that Paf1 defined an alternative initiating form of Pol II (Shi et al., 1997). However, other genetic and biochemical associations link Paf1C to several stages of mRNA production. For example, Ccr4, the major yeast deadenylase (Tucker et al., 2001), associates with Paf1C, and ccr4Δ strains share many phenotypes with paf1Δ, cdc73Δ, and ctr9Δ (Chang et al., 1999). Hpr1, linked to transcriptional elongation and nuclear export of mRNAs (Chavez and Aguilera 1997, Libri et al. 2002, Schneiter et al. 1999 and Zenklusen et al. 2002), is also found in association with Paf1C, and hpr1Δ, paf1Δ, and cdc73Δ strains share a hyperrecombination phenotype (Chang et al., 1999). Finally, Spt5, a known elongation factor (Hartzog et al., 1998), has been found in the same Pol II complex with Paf1, Ctr9, Cdc73, Rtf1, and Leo1 (Krogan et al. 2002, Mueller and Jaehning 2002 and Squazzo et al. 2002). Also linking Paf1C to several stages of mRNA synthesis are the observations that Rtf1 is important both for transcript start site selection (Stolinski et al., 1997) and for elongation (Costa and Arndt, 2000). Consistent with roles in more than one transcriptional stage, Paf1C components are found both at promoters and throughout the coding regions of genes (Pokholok et al. 2002 and Simic et al. 2003).

Loss of Paf1 or Ctr9 results in nearly identical severe phenotypes affecting many different cellular processes (Betz et al., 2002). Although many of these phenotypes can be correlated with reduced abundance of specific transcripts, the major function of Paf1C in mRNA metabolism is not yet clear. Recently, Paf1, Ctr9, and Rtf1 have been shown to be required for histone H2B ubiquitylation and for the subsequent histone H3 methylation by methyltransferases (Gerber and Shilatifard, 2003). However, the reported chromatin distribution of the methyltransferases is very different than that of Paf1, and loss of histone methylation does not result in phenotypes of equivalent severity to those of Paf1 factor mutations. This suggests that Paf1C must have additional roles in the cell. (Mueller et al. Molecular Cell, Vol. 14, 447-456, May 21, 2004).

Leo1, Paf1/RNA Polymerase II Complex Component, Homolog (*S. Cerevisiae*), also known as Leo1, RDL, Replicative Senescence Down-Regulated Leo1-Like Protein, or RNA Polymerase-Associated Protein LEO1, is a member of the Paf1 complex.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The invention will now be further described with reference to the following Example.

EXAMPLES

Forward Genetic Screen

To identify putative suppressors of siRNA-mediated heterochromatin formation the inventors performed a Small-RNA Mediated Silencing (sms) forward genetic screen.

They constructed a reporter strain (sms0), which expresses an RNA hairpin (ade6-hp) that is complementary to 250 nt of ade6+ from the nmt1+ locus on chromosome 1. Because it was previously reported that siRNA-mediated heterochromatin formation on a ura4+ reporter gene inserted at the trp1+ locus is possible if the heterochromatin protein Swi6 (HP1) is overexpressed (Iida, T., Nakayama, J. & Moazed, D. Mol Cell 31, 178-189, doi:S1097-2765(08) 00464-4 [pii]10.1016/j.molce1.2008.07.003 (2008)), they inserted a functional ade6+ gene at the trp1+ locus on chromosome 2 in the sms0 strain. They chose ade6+ as a reporter because ade6 mutant cells form red colonies on limiting adenine indicator plates, whereas ade6+ cells appear white. Although the ade6-hp construct generated siRNAs complementary to ade6+ mRNAs, no red colonies were visible, demonstrating that ade6+ siRNAs cannot silence the ade6+ gene in trans in sms0 cells. Even overexpression of Swi6 did not result in repression of the trp1+::ade6+ reporter. Further confirming the inability of ade6+ siRNAs to silence ade6+ expression in trans, ade6+ mRNA levels remained unaffected.

To screen for mutants that would enable ade6+ siRNAs to act in trans, the present inventors mutagenized sms0 cells with ethylmethansulfonat (EMS). To select against loss-of-function mutations in the adenine biosynthesis pathway, they tested red colonies for growth in the absence of adenine, resulting in 10 mutants that they named sms1-10. The red phenotype segregated through four successive backcrosses for all 10 mutants, but only in 5 mutants (sms1, sms3, sms4, sms6, sms8) was the red phenotype dependent on Dcr1 and the ade6+ reporter gene became H3K9 methylated. Thus, this sms screen uncovered five mutants that are highly susceptible for de novo formation of heterochromatin by siRNAs that are acting in trans.

To map the mutations in sms mutants the inventors re-sequenced the genomes of sms0 and the backcrossed sms1-10 mutants using whole-genome next generation sequencing. They found that all Dcr1-independent mutants had mutations in either the ade6+ or the ade7+ gene. Because these mutants grow in the absence of adenine, these mutations constitute weak loss-of-function alleles in the adenine biosynthesis pathway. In the Dcr1-dependent mutants they mapped missense or nonsense mutations in the genes SPBC651.09c, SPAC664.03, SPBC13E7.08c, and SPBC17G9.02c, whose homologues in budding yeast encode for protein subunits of the RNA polymerase-associated factor 1 complex (Paf1C). They therefore named SPAC664.03, SPBC13E7.08c, and SPBC17G9.02c after the S. cerevisiae homologues paf1+, leo1+, and cdc73+, respectively. Because rtf1+ has already been assigned to another S. pombe gene, we refer SPBC651.09c to as Repressor Of Trans-silencing 1 (rot1+).

siRNA-Directed Heterochromatin Formation

The inventors next reconstituted the candidate point mutations in Paf1, Leo1, Cdc73, and Rot1 in cells containing the trp1+::ade6+ reporter. All five point mutations recapitulated the sms mutant phenotype in cells expressing ade6-hp siRNAs. As expected from the red color assays, ade6+ mRNA levels were reduced in all mutant strains. Importantly, expression of trp1+::ade6+ remained unaffected in the absence ade6-hp siRNAs, demonstrating that ade6+ silencing on chromosome 2 does not result from impaired transcription in the Paf1C mutants but is specifically initiated by ade6+ siRNAs encoded on chromosome 1. siRNA-mediated trp1+::ade6+ silencing was also observed in cells that express a C-terminally 3×FLAG tagged version of the fifth Paf1C subunit Tpr1. Thus, the inventors have identified mutant alleles for the homologs of all five subunits of Paf1C that enable siRNAs to induce gene silencing in trans.

It has been previously shown that the endogenous wild type ura4+ gene is refractory to silencing by siRNAs acting in trans (Simmer, F. et al. EMBO reports 11, 112-118, doi:10.1038/embor.2009.273 (2010); Iida, T., Nakayama, J. & Moazed, D. Mol Cell 31, 178-189, doi:S1097-2765(08) 00464-4 [pii]10.1016/j.molce1.2008.07.003 (2008); Yu, R., Jih, G., Iglesias, N. & Moazed, D. Molecular cell 53, 262-276, doi:10.1016/j.molce1.2013.11.014 (2014)). Therefore, The inventors introduced the paf1-Q264Stop mutation in a strain expressing ura4+ siRNAs from a ura4+ hairpin integrated at the nmt1+ locus (Yu, R., Jih, G., Iglesias, N. & Moazed, D. Molecular cell 53, 262-276, doi:10.1016/j.molce1.2013.11.014 (2014)) and monitored ura4+ repression by growing cells on media containing 5-Fluoroorotic Acid (5-FOA). As expected, paf1+ cells did not grow on 5-FOA containing media, indicating expression of the ura4+ gene. However, paf1-Q264Stop cells were able to form colonies on 5-FOA containing media, demonstrating siRNA-directed silencing of the endogenous ura4+ locus. Similarly, siRNAs generated at the heterochromatic ura4+:: 5BoxB locus (Buhler, M., Verdel, A. & Moazed, D. Cell 125, 873-886 (2006)) were able to silence a leu1delta::ura4+ reporter in trans in paf1-Q264Stop but not paf1+ cells. Finally, they also observed silencing of the endogenous ade6+ gene if ade6-hp siRNAs were expressed from the nmt1+ locus in paf1-Q264Stop cells. In summary, Paf1C mutations enabled siRNA-directed silencing in trans at all of the many euchromatic loci that they tested.

The foregoing results hence indicate de novo formation of heterochromatin can be mediated by trans-acting siRNAs. Indeed, Paf1C mutants showed high H3K9 methylation at all ade6+ siRNA target loci, demonstrating that Paf1C prevents trans- as well as cis-acting siRNAs from directing methylation of H3K9. Further corroborating the formation of bona fide heterochromatin at the ade6+ target locus, ade6+ repression was dependent on components of the SHREC and CLRC complexes, as well as the HP1 proteins Swi6 and Chp2. Finally, the formation of heterochromatin reduced transcriptional activity of the ade6+ target locus as evidenced by reduced H3K36 tri-methylation and RNA polymerase II occupancy. From these results the inventors conclude that siRNAs are sufficient to initiate the formation of heterochromatin, but that this is under strict negative control by Paf1C.

Epigenetic Gene Silencing

Consistent with the formation of an epigenetically distinct chromatin domain at the siRNA target loci, cells in a population of freshly generated Paf1C mutants were either fully red or white. The latter gradually became red with increasing numbers of mitotic divisions and once established, the silent state was remarkably stable. The fact that not all cells in a population of naïve Paf1C mutant cells turned red immediately allowed us to determine the frequency of initiation of heterochromatin formation quantitatively. This analysis revealed that silencing in mitotic cells was efficiently established in leo1-W157Stop mutant cells, whereas cdc73-G313R cells were the least efficient. Descendants of a red colony switched to the white phenotype only sporadically in all Paf1C mutants, demonstrating that maintenance of heterochromatin is very robust in these cells.

Interestingly, siRNA-directed de novo formation of heterochromatin was most efficient in meiosis. In 70% of all crosses between a naïve paf1-Q264Stop mutant (white) and a paf1+ cell, at least one of two paf1-Q264Stop spores had initiated ade6+ repression (red). The inventors also observed highly efficient propagation of the silent state through meiosis, but only in descendants of spores that inherited the Paf1C mutation. Thus, siRNAs are sufficient to initiate the formation of very stable heterochromatin if Paf1C function is impaired.

Assembly of heterochromatin at the ade6+ target gene was accompanied by the production of novel ade6+ siRNAs that are not encoded in the ade6-hp. Thus, primary ade6-hp siRNAs trigger the production of highly abundant secondary ade6+ siRNAs in Paf1C mutant strains. To test whether continuous production of siRNAs is necessary for sustaining the repressed state, the inventors deleted genes coding for RNAi factors and found that silencing of the ade6+ target gene was completely abolished in all canonical RNAi mutants. Deletion of tri1+ resulted in moderate derepression of ade6+ silencing, suggesting a minor contribution of this exonuclease to siRNA-mediated heterochromatin silencing. To test whether secondary siRNAs produced at the ade6+ target locus are sufficient to maintain heterochromatin, they crossed a trp1+::ade6+paf1-Q264Stop ade6-hp+ strain (red) with a trp1+::ade6+ paf1-Q264Stop (white) strain. These crosses regularly produced spores that gave rise to red cells even in the absence of the nmt1+::ade6-hp+ allele. The red phenotype was still visible after replica plating, demonstrating that heterochromatin can be maintained in the absence of the primary siRNAs for hundreds of mitotic cell divisions.

In summary, these results demonstrate that siRNAs can induce an epigenetic change in gene expression in meiotic and mitotic cells. Whereas a functional RNAi machinery is required to initiate and maintain repression, secondary siRNA production is sufficient to propagate the repressed state for many mitotic cell divisions independently of the primary siRNAs that triggered the epigenetic switch.

Formation of Facultative Heterochromatin

To assess the impact of the Paf1C mutations on genome expression, the inventors hybridized total RNA to whole-genome tiling arrays. They included the parental wild type strain, all Paf1C point mutations discovered in their screen, and full deletions of the paf1+ and leo1+ genes in their analysis. Comparison of the genome-wide expression profiles of two biological replicates each strain revealed that cdc73-G313R and paf1delta cells are most different from wild type cells. All the other mutants, including leo1delta, were very similar to wild type, demonstrating that general transcription remains largely unaffected in these mutants. Therefore, paf1-G104R, paf1-Q264Stop, rot1-Q472Stop, and leo1-W157Stop can be considered as separation-of-function alleles that solely impair repression of heterochromatin formation. Intriguingly, leo1delta belongs to the same cluster of mutants, indicating that Leo1 is not required for canonical Paf1C activities in S. pombe. Rather, Leo1 might exclusively function to prevent siRNA-mediated heterochromatin formation. Consistent with this assumption, growth of rot1delta, paf1delta, tpridelta, and cdc73delta cells is severely retarded, whereas leo1delta cells are indistinguishable from wild type cells. Furthermore, ade6-hp siRNAs repressed the trp1+::ade6+ locus in leo1delta cells. These results point to Leo1 as a bona fide repressor of small RNA-mediated heterochromatin formation.

The inventors next investigated whether Paf1C mutant cells would disclose genomic regions that could be potentially assembled into facultative heterochromatin by endogenous siRNAs. Based on their results, loci at which facultative heterochromatin forms in an RNAi-dependent manner are expected to display reduced RNA expression with a concomitant increase in siRNA production. As expected, the nmt1+::ade6-hp+, trp1+::ade6+, and ade6-704 loci fulfilled this criteria. Moreover, they observed repression and siRNA production for genes flanking these loci, indicating spreading of heterochromatin into neighboring genes, which occurred up to 6 kb up or downstream of the ade6-hp siRNA target sites. In addition to these regions, the inventors observed siRNA-directed silencing signatures at different, non ade6+-linked genomic loci, indicating that Paf1C may function to protect the S. pombe genome from spurious repression of protein coding genes by endogenous siRNAs. Notably, the inventors did not recover the same sites repeatedly in the different Paf1C mutants. This implies that initiation of silencing at these sites occurred stochastically and that there are no specific sites primed for the formation of facultative heterochromatin in mitotic cells that are grown under standard laboratory conditions.

MATERIALS AND METHODS

Strains, Plasmids:

Fission yeast strains were grown at 30° C. in YES medium. All strains were constructed following a PCR-based protocol (Bahler, J. et al. *Yeast* 14, 943-951 (1998)) or by standard mating and sporulation.

EMS Mutagenesis, Hit Selection, and Backcrossing:

Exponentially growing sms0 (SPB464) cells were washed and resuspended in 50 mM K-phosphate buffer (pH7.0) and treated with EMS (final concentration 2.5%) for 150 min. An equal volume of freshly prepared 10% Na-thiosulfate was then added. Cells were washed with water and subsequently resuspended in YES. EMS treatment resulted in ~50% cell viability. To screen for mutants in which ade6+ expression was silenced, cells were spread on YE plates. About 350000 colonies were examined and pink colonies were selected for further evaluation. Positive hits were backcrossed 4 times with the parental strains SPB464 or SPB1788, depending on mating type.

Silencing Assays:

To assess ura4+ expression, serial 10-fold dilutions of the respective strains were plated on PMGc (nonselective, NS) or on PMGc plates containing 2 mg/ml 5-FOA. To assess ade6+ expression, serial 10-fold dilutions of the respective strains were plated on YES and YE plates.

Assessment of Initiation Versus Maintenance of Ectopic Heterochromatin Formation:

Mutant strains were seeded on YE plates and single cell-derived red or white colonies were selected. Colonies were resuspended in water and 100-500 cells were seeded on YE plates, which were then incubated at 30° C. for 3 days. Images of the plates were acquired after one night at 4° C. and colonies were counted automatically using Matlab (The MathWorks) and ImageJ Software (NIH).

RNA Isolation and cDNA Synthesis:

RNA isolation and cDNA synthesis was performed as described in Emmerth, S. et al. (*Developmental cell* 18, 102-113 (2010)).

Quantitative Real-Time PCR:

Real-time PCR on cDNA samples and ChIP DNA was performed as described in Keller, C. et al. (*Molecular cell* 47, 215-227 (2012)) using a Bio-Rad CFX96 Real-Time System using SsoAdvanced SYBR Green supermix (Bio-Rad).

Chromatin Immunoprecipitation (ChIP):

ChIP experiments were performed as previously described in Keller, C. et al. (*Molecular cell* 47, 215-227 (2012)) with minor modifications. Briefly, *S. pombe* cells were fixed with 1% formaldehyde for 15 min and then lysed in buffer containing 50 mM HEPES/KOH, pH 7.5, 140 mM NaCl, 1 mM EDTA, 1% Triton X-100, 0.1% Na deoxycholate, 1 mM PMSF and protease-inhibitor cocktail. Chromatin was sheared with a Bioruptor (Diagenode). The following antibodies were used in this study: histone H3K9me2-specific mouse monoclonal antibody from Wako (clone no. MABI0307), histone H3-specific rabbit polyclonal antibody from Abcam (clone no. ab1791), histone H3K36me3-specific rabbit polyclonal antibody from Abcam (clone no. ab9050), and RNA Polymerase II mouse monoclonal antibody from Covance (clone no. 8WG16).

Small RNA Sequencing:

Total RNA was isolated from exponentially growing cells using the hot phenol method (Leeds, P., Peltz, S. W., Jacobson, A. & Culbertson, M. R. *Genes Dev.* 5, 2303-2314 (1991)). The RNA was fractionated using RNeasy Midi columns (Qiagen) following the 'RNA cleanup protocol' provided by the manufacturer. The flow-through fraction was precipitated ('small RNA' fraction). Aliquots (25 micrograms) of the small RNA fraction were separated by 17.5% PAGE and the 18- to 28-nt population purified. Libraries were prepared using the Illumina TruSeq™ small RNA preparation protocol (Cat.# RS-930-1012). The 145- to 160-nt population was isolated and the library sequenced on an Illumina HiSeq2000. Small RNA reads were aligned as described previously in Emmerth, S. et al. (*Developmental cell* 18, 102-113 (2010)) with two mismatches allowed.

Whole Genome Sequencing:

Cells form overnight culture were harvested, washed once with water and flash frozen in liquid nitrogen. Cells were spheroplasted in spheroplast buffer (1.2 M sorbitol, 100 mM KHPO4, pH 7.5, 0.5 mg ml$^{-1}$ Zymolyase (Zymo Research), 1 mg ml$^{-1}$ lysing enzyme from *Trichoderma harzianum* (Sigma)). Genomic DNA was isolated using the DNeasy Blood and Tissue Kit (Qiagen). Barcoded genomic DNA libraries for Illumina next-generation sequencing were prepared from 50 ng genomic DNA using the Nextera DNA Sample Preparation Kit (Illumina, San Diego, USA). Libraries were pooled equimolarly and sequenced on one lane of a HiSeq2000 machine (Illumina). Basecalling was done with RTA 1.13.48 (Illumina) software and for the demultiplexing CASAVA_v1.8.0 (Illumina) was used. For each strain, between 8.7 and 25.5 Mio. (mean of 14.2 Mio) 50-mer reads were generated and aligned to the *Schizosaccharomyces pombe* 972h-genome assembly (obtained on Sep. 17, 2008 from http://www.broad.mit.edu/annotation/genome/schizosaccharomyces_group/MultiDownloads.html) using "bwa" (Li, H. & Durbin, R. *Bioinformatics* 25, 1754-1760 (2009), version 0.7.4) with default parameters, but only retaining single-hit alignments ("bwa samse-n1" and selecting alignments with "X0:i:1"), resulting in a genome coverage between 26 and 85-fold (mean of 44-fold). The alignments were converted to BAM format, sorted and indexed using "samtools" (Li, H. et al. *Bioinformatics* 25, 2078-2079 (2009), version 0.1.19). Potential PCR duplicates were removed using "MarkDuplicates" from "Picards" (http://picard.sourceforge.net/, version 1.92). Sequence variants were identified using GATK (DePristo, M. A. et al. *Nature genetics* 43, 491-498 (2011), version 2.5.2) indel realignment and base quality score recalibration using a set of high confidence variants identified in an initial step as known variants, followed by SNP and INDEL discovery and genotyping for each indivial strain using standard hard filtering parameters, resulting in a total of 270 to 274 sequence variations (mean of 280) in each strain compared to the reference genome (406 unique variations in total over all strains).

Finally, variations were filtered to retain only high quality single nucleotide variations (QUAL>=50) of EMS-type (G|C to A|T) with an alellic balence>=0.9 (homozygous) that were not also identified in the parental strain (sms0), reducing the number of variations per strain to a number between 2 and 8 (mean of 4.6).

Expression Profiling:

RNA was isolated from cells collected at OD600=0.5 using the hot phenol method (Leeds, P., Peltz, S. W., Jacobson, A. & Culbertson, M. R. *Genes Dev.* 5, 2303-2314 (1991)).

The isolated RNA was processed according to the GeneChip Whole Transcript (WT) Double-Stranded Target Assay Manual from Affymetrix using the GeneChip *S. pombe* Tiling 1.0FR. All tiling arrays were processed in R (Ihaka R, G. R. *Journal of Computational and Graphical Statistics.* 5, 299-314 (1996)) using Bioconductor (Gentleman, R. C. et al. *Genome Biol* 5, R80 (2004)) and the packages tilingArray (Huber, W., Toedling, J. & Steinmetz, L. M. *Bioinformatics* 22, 1963-1970 (2006)) and preprocessCore. The arrays were RMA background-corrected, quantile-normalized, and log 2-transformed on the oligo level using the following command: expr←log 2(normalize.quantiles(rma.background.correct(exprs(readCel2eSet (filenames,rotated=TRUE))))). Oligo coordinates were intersected with the genome annotation and used to calculate average expression levels for individual genomic features (excluding those with <10 oligos) as well as broader annotation categories. In the latter case, multimapping oligos were counted only once per category (avoiding multiple counts from the same oligo).

Gene Nomenclature:

The proteins Paf1, Cdc73, Rtf1, Leo1, and Ctr9 form a stable complex in *S. cerevisiae* (Paf1C). The systematic IDs of the genes encoding the *S. pombe* homologs of these proteins are SPAC664.03, SPBC17G9.02c, SPBC651.09c, SPBC13E7.08c, and SPAC27D7.14c, respectively. The Ctr9 homolog SPAC27D7.14c is currently annotated as Tpr1. The Rtf1 homolog SPBC651.09c is currently annotated as PAF-Related Factor 1 (prf1+), because rtf1+ is already used for an unrelated gene (SPAC22F8.07c). The inventors prefer to refer SPBC651.09c to as Repressor Of Trans-silencing 1 (rot1+) because it better describes its function. Therefore, they refer SPAC664.03, SPBC17G9.02c, SPBC651.09c, SPBC13E7.08c, and SPAC27D7.14c to as paf1+, cdc73+, rot1+, leo1+, and tpr1+, respectively, in this description.

The invention claimed is:

1. A method for the targeted formation of heterochromatin and epigenetic silencing at a site in the genome of an animal cell, wherein the site encodes an expressed RNA, said method comprising inhibiting the Paf1 complex in the cell and contacting the cell with a small RNA that is sufficiently complementary to a 5'-region of the expressed RNA to hybridize to it under physiological conditions, wherein the method induces heterochromatin formation and epigenetic gene silencing in said site, and wherein the expressed RNA does not encode any component of the Paf1 complex.

2. The method of claim 1, wherein the step of inhibiting the Paf1 complex comprises the step of inhibiting a component of the Paf1 complex selected from Paf1, Cdc73, Rtf1, Leo1, and Ctr9.

3. The method of claim 1, wherein the step of inhibiting the Paf1 complex comprises the step of selecting a mutant cell in which at least one gene of a component of the Paf1 complex is mutated in such a way that the expression of the at least one gene of a component of the Paf1 complex is reduced.

4. The method of claim 3 wherein said mutant is a naturally-occurring mutant.

5. The method of claim 2, wherein said component of the Paf1 complex is Leo 1.

6. The method of claim 2, wherein the expression of said component of the Paf1 complex is reduced.

7. The method of claim 3, wherein said component of the Paf1 complex is selected from Paf1, Cdc73, Rtf1, Leo1, and Ctr9.

8. The method of claim 1, wherein said method is carried out in vitro, in vivo or ex vivo.

* * * * *